United States Patent [19]
Crowley

[11] Patent Number: 5,984,861
[45] Date of Patent: Nov. 16, 1999

[54] ENDOFLUORESCENCE IMAGING MODULE FOR AN ENDOSCOPE

[75] Inventor: Robert J. Crowley, Sudbury, Mass.

[73] Assignee: Boston Scientific Corporation, Natick, Mass.

[21] Appl. No.: 08/939,706

[22] Filed: Sep. 29, 1997

[51] Int. Cl.⁶ ..................................................... A61B 1/06
[52] U.S. Cl. ......................... 600/175; 600/179; 600/181; 600/476
[58] Field of Search ..................................... 600/101, 160, 600/175, 176, 181, 179, 407, 476; 250/339.07, 372

[56] References Cited

U.S. PATENT DOCUMENTS

| | | | |
|---|---|---|---|
| 2,002,559 | 5/1935 | Wappler | 174/39 |
| 2,583,937 | 1/1952 | Fossati | 128/4 |
| 3,176,114 | 3/1965 | Kneisley | 219/223 |
| 3,593,706 | 7/1971 | Schubert | 600/179 |
| 4,233,493 | 11/1980 | Nath | 219/354 |

(List continued on next page.)

FOREIGN PATENT DOCUMENTS

| | | |
|---|---|---|
| 0 314 937 | 10/1988 | European Pat. Off. . |
| 0 304 321 | 9/1992 | European Pat. Off. . |
| 0 629 380 | 12/1994 | European Pat. Off. . |
| 0 650 694 A1 | 5/1995 | European Pat. Off. . |
| 0 728 440 | 8/1996 | European Pat. Off. . |
| 0 777 119 | 6/1997 | European Pat. Off. . |
| 0 792 618 | 9/1997 | European Pat. Off. . |
| 888727 | 7/1949 | Germany . |
| 30 23 130 | 1/1982 | Germany . |
| 40 05 743 | 8/1991 | Germany . |
| 195 12 518 | 10/1995 | Germany . |
| 2-223828 | 9/1990 | Japan . |
| 7-88105 | 4/1995 | Japan . |
| 7-289506 | 11/1995 | Japan . |
| 8-83569 | 3/1996 | Japan . |
| 9-192138 | 7/1997 | Japan . |
| WO 90/04352 | 5/1990 | WIPO . |
| WO 90/12536 | 11/1990 | WIPO . |
| WO 91/15151 | 10/1991 | WIPO . |
| WO 92/14514 | 9/1992 | WIPO . |
| WO 92/15253 | 9/1992 | WIPO . |
| WO 94/13191 | 6/1994 | WIPO . |
| WO 95/12349 | 5/1995 | WIPO . |
| WO 96/05693 | 2/1996 | WIPO . |
| WO 96/07451 | 3/1996 | WIPO . |
| WO 96/24406 | 8/1996 | WIPO . |
| WO 96/39932 | 12/1996 | WIPO . |
| WO 97/01985 | 1/1997 | WIPO . |
| WO 98/22805 | 5/1998 | WIPO . |

OTHER PUBLICATIONS

International Search Report for PCT/US98/21100 dated Feb. 8, 1999.

Coleman et al., "Acoustic Emission and Sonoluminescence Due to Cavitation at the Beam Focus of an Electrohydraulic Shock Wave Lithotripter", *Ultrasound in Med. Biol,* vol. 18, No. 3, pp. 267–281 (1992).

Vona et al., "A Test of the Hypothesis that Cavitation at the Focal Area of an Extracorporeal Shock Wave Lithotripter Produces Far Ultraviolet and Soft X–Ray Emissions", *J. Acoust. Soc. Am.,* vol. 98 (2), pp. 706–711, (Aug. 1995).

Cothren et al., "Gastrointestinal Tissue Diagnosis by Laser–Induced Fluorescence Spectroscopy at Endoscopy" *Gastro Endoscopy,* vol. 36 No. 2, pp. 105–111, 1990.

Kapadia et al, "Laser–induced fluorescence spectroscopy of human colonic mucosa", *Gastroentrerology,* vol. 29, pp. 150–157, 1990.

(List continued on next page.)

*Primary Examiner*—John P. Leubecker
*Attorney, Agent, or Firm*—Testa, Hurwitz & Thibeault, LLP

[57] ABSTRACT

An endofluorescence module is utilized with an interventional device insertible in a body to provide at least one fluorescence excitation source. The module can be attached to the distal end of an endoscope, cystoscope or other optical imaging device. One or more filters are utilized to enhance the fluorescence response from the tissue under examination. A light shutter controls the exposure of an optical channel during operation. The adaptability and small size of the module correspond with low cost and disposability.

24 Claims, 5 Drawing Sheets

U.S. PATENT DOCUMENTS

| | | | |
|---|---|---|---|
| 4,274,706 | 6/1981 | Tangonan . | |
| 4,289,966 | 9/1981 | Roberts | 250/378 |
| 4,340,307 | 7/1982 | Diamond et al. | 356/418 |
| 4,472,728 | 9/1984 | Grant et al. | 357/30 |
| 4,528,986 | 7/1985 | Arundel et al. | 600/476 |
| 4,541,272 | 9/1985 | Bause | 73/118 |
| 4,548,505 | 10/1985 | Ono | 356/445 |
| 4,556,057 | 12/1985 | Hiruma et al. . | |
| 4,570,638 | 2/1986 | Stoddart et al. . | |
| 4,672,972 | 6/1987 | Berke | 128/653 |
| 4,718,417 | 1/1988 | Kittrell et al. | 128/303.1 |
| 4,821,117 | 4/1989 | Sekiguchi | 600/160 |
| 4,872,458 | 10/1989 | Kanshira et al. | 128/401 |
| 4,882,623 | 11/1989 | Uchikubo | 358/98 |
| 4,894,547 | 1/1990 | Leffell et al. . | |
| 4,895,138 | 1/1990 | Yabe | 600/179 |
| 4,902,896 | 2/1990 | Fertig, Sr. et al. | 290/348 |
| 4,916,534 | 4/1990 | Takahashi et al. | 600/181 |
| 4,928,172 | 5/1990 | Uchara et al. | 358/98 |
| 4,930,516 | 6/1990 | Alfano et al. . | |
| 4,938,602 | 7/1990 | May et al. | 356/435 |
| 4,981,138 | 1/1991 | Deckelbaum et al. | 128/665 |
| 5,001,556 | 3/1991 | Nakamura et al. | 358/98 |
| 5,009,655 | 4/1991 | Daignault, Jr. et al. | 606/7 |
| 5,021,888 | 6/1991 | Kondou et al. | 358/213.11 |
| 5,034,010 | 7/1991 | Kittrell et al. . | |
| 5,036,853 | 8/1991 | Jeffcoat et al. . | |
| 5,042,494 | 8/1991 | Alfano | 128/665 |
| 5,045,056 | 9/1991 | Behl | 604/49 |
| 5,056,503 | 10/1991 | Nagasaki et al. | 128/6 |
| 5,062,428 | 11/1991 | Chance . | |
| 5,106,387 | 4/1992 | Kittrell et al. . | |
| 5,115,137 | 5/1992 | Andersson-Engels et al. . | |
| 5,116,759 | 5/1992 | Klainer et al. | 435/288 |
| 5,125,404 | 6/1992 | Kittrell et al. . | |
| 5,127,407 | 7/1992 | Tan . | |
| 5,131,398 | 7/1992 | Alfano et al. . | |
| 5,166,755 | 11/1992 | Gat | 356/419 |
| 5,172,693 | 12/1992 | Doody . | |
| 5,174,297 | 12/1992 | Daikuzono . | |
| 5,187,572 | 2/1993 | Nakamura et al. | 358/98 |
| 5,187,672 | 2/1993 | Chance et al. . | |
| 5,193,542 | 3/1993 | Missanelli et al. . | |
| 5,197,470 | 3/1993 | Helfer et al. . | |
| 5,201,318 | 4/1993 | Rava et al. . | |
| 5,206,174 | 4/1993 | Gehrke et al. | 436/58 |
| 5,213,569 | 5/1993 | Davis . | |
| 5,222,477 | 6/1993 | Lia | 600/111 |
| 5,233,621 | 8/1993 | Lawandy | 372/22 |
| 5,242,437 | 9/1993 | Everett et al. | 606/15 |
| 5,261,410 | 11/1993 | Alfano et al. . | |
| 5,262,645 | 11/1993 | Lambert et al. | 250/339 |
| 5,304,173 | 4/1994 | Kittrell et al. . | |
| 5,305,748 | 4/1994 | Wilk . | |
| 5,309,907 | 5/1994 | Fang et al. | 128/633 |
| 5,318,024 | 6/1994 | Kittrell et al. | 128/634 |
| 5,348,018 | 9/1994 | Alfano et al. . | |
| 5,350,375 | 9/1994 | Deckelbaum et al. . | |
| 5,351,532 | 10/1994 | Hager | 73/153 |
| 5,377,676 | 1/1995 | Vari et al. | 128/634 |
| 5,383,467 | 1/1995 | Auer et al. . | |
| 5,386,827 | 2/1995 | Chance et al. . | |
| 5,398,844 | 3/1995 | Zaslavsky et al. | 221/208 |
| 5,402,778 | 4/1995 | Chance . | |
| 5,402,792 | 4/1995 | Kimura . | |
| 5,405,369 | 4/1995 | Selman et al. | 607/88 |
| 5,413,108 | 5/1995 | Alfano . | |
| 5,417,207 | 5/1995 | Young et al. | 128/634 |
| 5,419,323 | 5/1995 | Kittrell et al. . | |
| 5,421,337 | 6/1995 | Richards-Kortum et al. . | |
| 5,421,339 | 6/1995 | Ramanujam et al. . | |
| 5,445,608 | 8/1995 | Chen et al. | 604/20 |
| 5,452,723 | 9/1995 | Wu et al. . | |
| 5,456,252 | 10/1995 | Vari et al. . | |
| 5,461,229 | 10/1995 | Sauter et al. | 250/253 |
| 5,467,767 | 11/1995 | Alfano et al. | 128/665 |
| 5,512,757 | 4/1996 | Cederstrand et al. . | |
| 5,517,313 | 5/1996 | Colvin, Jr. . | |
| 5,542,928 | 8/1996 | Evans et al. | 604/113 |
| 5,545,897 | 8/1996 | Jack . | |
| 5,553,614 | 9/1996 | Chance . | |
| 5,555,885 | 9/1996 | Chance . | |
| 5,556,421 | 9/1996 | Prutchi et al. | 607/36 |
| 5,562,100 | 10/1996 | Kittrell et al. . | |
| 5,571,152 | 11/1996 | Chen et al. | 607/92 |
| 5,579,773 | 12/1996 | Vo-Dinh et al. . | |
| 5,632,740 | 5/1997 | Koch et al. . | |
| 5,647,368 | 7/1997 | Zeng et al. | 126/665 |
| 5,769,791 | 6/1998 | Benaron et al. . | |
| 5,785,658 | 7/1998 | Benaron et al. . | |
| 5,807,261 | 9/1998 | Benaron et al. | 600/476 |

OTHER PUBLICATIONS

Lilge et al., "Light Induced Fluorescennce Spectroscopy at Endoscopy", Presented at the 10th Asisan Pacific Congress of Gastroenterology, 1996.

Huang et al., "Fluorescence Diagnosis of Gynecological Cancerous and Normal Tissues", *SPIE*, vol. 2135, pp. 42–44, 1994.

Anidjar et al., "Ultraviolet Laser–Induced Autofluorescence Distinction Between Malignant and Normal Urothelial Cells and Tissues", *Journal of Biomedical Optics,* vol. 1 No. 3, pp. 335–341, 1996.

Crowley et al., "Ultrasound Guided Therapeutic Catherters: Recent Developments and Clinical Results", *The International Journal of Cardiac Imaging*, vol. 6, pp. 145–156, 1991.

Meindi, J. Implantable Telemetry in Biomedical Research, Electronics Engineers' Handbook, McGraw–Hill 1989, pp. 26–41—25–53.

Ko, Biomedical Sensors and Actuators, Electronics Engineers' Handbook, McGraw–Hill 1989, pp. 26–53—26–68.

International Search Report for PCT/US97/20367.

International Search Report for PCT/US97/20435.

Petrofsky, "In Vivo Measurrement of Brain Blood Flow in the Cat," *IEEE Transactions on Biomedical Engineering;* vol. BME–26, No. 8:441–445 (Aug., 1979).

Internet Publication, http://iqe.ethz.ch/–fpst/Final_Report/M4/M4PO4–1.html.

Kopp et al., "Stay Tuned: Photonic Filters Color Your World," *Photonics Spectra,* Mar. 1997, pp. 125–129.

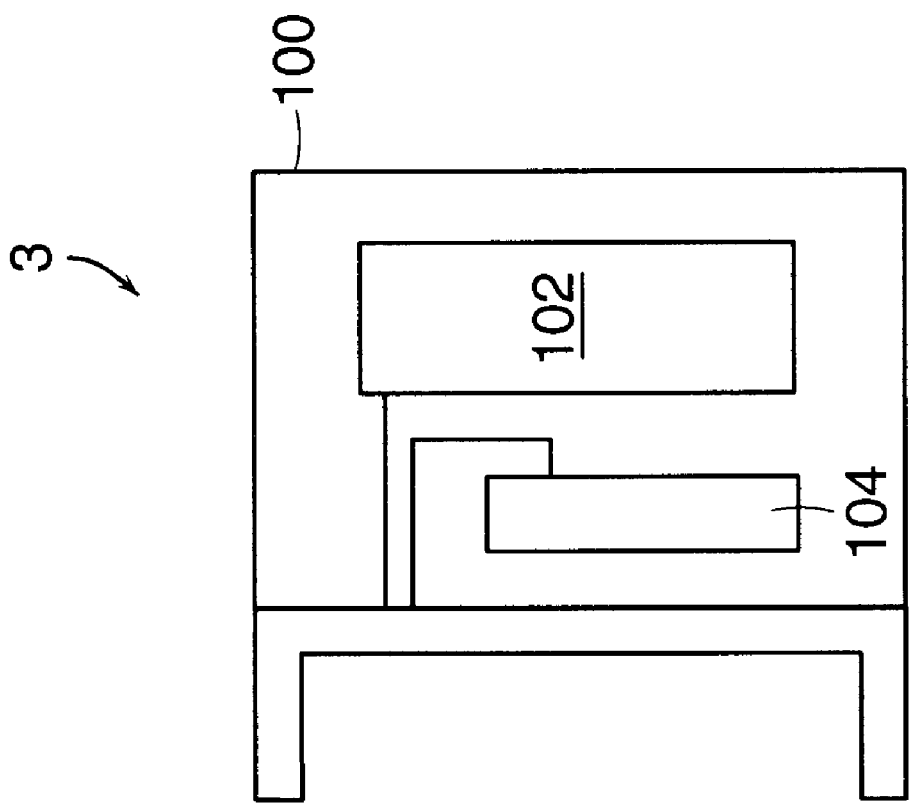

5,984,861

ENDOFLUORESCENCE IMAGING MODULE FOR AN ENDOSCOPE

FIELD OF THE INVENTION

The invention relates generally to an apparatus and method for performing diagnostic procedures in a body. In particular, the invention relates to a diagnostic module attachable to the distal end of an interventional device for performing endofluorescence imaging of tissue in a body.

BACKGROUND OF THE INVENTION

Fluorescence-enhanced endoscopic examination of tissue typically involves an endoscope having a light source (e.g., a laser) and imaging sensors, which include filters that pass specific wavelengths associated with displasia or cancerous tissue. First, an operator obtains a white light image to locate a general area of tissue to be examined. Next, the operator actuates a second light source to illuminate the tissue with light having the appropriate wavelength(s) to produce a desired fluorescent emission from the tissue. Such endoscopes are necessarily more complex and costly than conventional endoscopes in that they require additional light sources, external control electronics and display systems, and light guides capable of transmitting ultraviolet (UV) wavelengths that are often important for fluorescence tissue spectroscopy purposes. Also, such endoscopes are inherently costly and must be carefully recycled and cleaned after each use. Recycling places a burden upon hospitals to maintain multiple endoscopes so that at least one of the various styles, lengths and types can be available for use at a given time.

SUMMARY OF THE INVENTION

It is therefore a principle object of the invention to provide a means for modifying a conventional endoscope so that it can be used to perform tissue spectroscopy. It is another object of the invention to provide a reversible means for modifying the endoscope so that it can be easily restored to its normal configuration without damage or the need for adjustments. It is yet another object of the invention to provide an attachment that can be attached immediately prior to use of such endoscope so that the user would have no need to prepare, expend or contaminate endoscopic equipment needlessly. It is yet another object of the invention to provide a low cost attachment that can be used with a wide variety of endoscopes and can modify input and output light from/to the endoscope so that fluorescence images can be produced easily, quickly and inexpensively.

An endofluorescence imaging module has been developed which is useful with a variety of interventional devices including, without limitation, endoscopes and cystoscopes. The module includes a housing which can be attached to the distal end of the interventional device. One or more light sources are disposed in the housing for illuminating tissue within the body. A light modulator is disposed in the housing for modifying the light emitted by at least one of the light sources.

In one embodiment, the housing includes an optically transparent region to pass the light originating from the light sources and received from the tissue. Light sources can include, without limitation, light emitting diodes, lasers, pulsed light sources, sources of ultraviolet energy, or a flashlamp.

The light modulator can include a filter providing a range of wavelengths to the optical channel of the interventional device. The filter can be an acousto-optic tunable filter, interference filter, grating, prism, holographic filter, or other component that provides a spectral passband. The light modulator also includes a shutter, which can be a liquid crystal device. In another embodiment, the light signal can be controlled by a signal corresponding to the operation of the flashlamp. In another embodiment, a control unit attaches to the proximal end of the interventional device. The control unit provides electrical power and control signals for operation of the light sources and detector in the module.

The invention also features a method for performing endofluorescence imaging of tissue in a body. The method includes attaching a housing having at least one light source and a light modulator to the distal end of an endoscope. The method further includes illuminating the tissue using at least one of the light sources. In one embodiment, the method includes transmitting pulses of optical energy. In another embodiment, the method includes controlling the exposure of the optical channel of the endoscope. In another embodiment, the method includes spectrally filtering the optical energy from the tissue. In another embodiment, the method further comprises the steps of: providing a control unit having a power supply and control electronics; attaching the control unit to the proximal end of an endoscope; and providing electrical power and control signals to the light source and detector.

BRIEF DESCRIPTION OF THE DRAWINGS

FIG. 4A is a schematic diagram of a cross-sectional view of an endofluorescence imaging module which can be removably attached to the distal end of an interventional device, according to the invention.

DETAILED DESCRIPTION OF THE INVENTION

Figure 1:
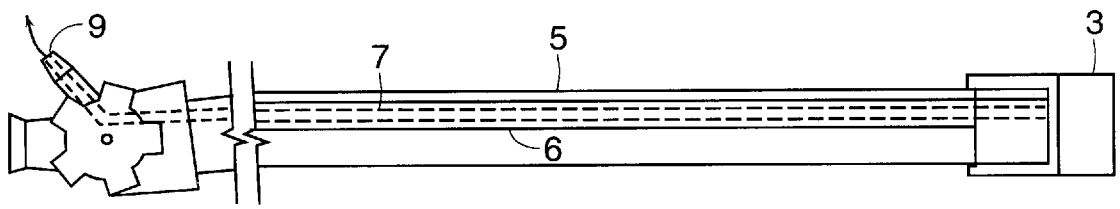
FIG. 1 is a side view of an endofluorescence imaging module mounted on the distal tip of an endoscope.

FIG. 1 is a side view of an endofluorescence imaging module 3 attached by friction fit to the distal tip of an endoscope 5. Control lines 7 carrying electrical power and control signals extend from the endofluorescence imaging module 3 back through the working channel 6 of the endoscope 5. The control lines 7 extend out the working channel spout 9.

Figure 2:
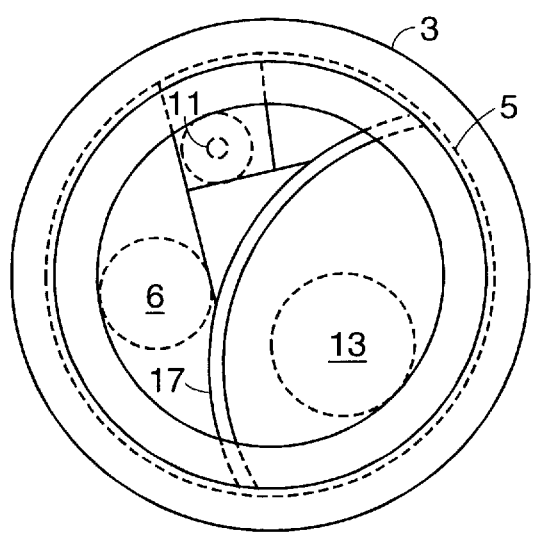
FIG. 2 is an end view of an endofluorescence imaging module.

FIG. 2 shows an end view of the imaging module 3 attached to the endoscope 5. An instrumentation mount 11 protrudes into the center of module 3. The mount 11 is positioned so as to not interfere with an optical channel 13 or working channel 6 of the endoscope 5. The imaging module 3 also includes a light modulator assembly 17 positioned over the optical channel 13. The optical channel 13 can be an optical fiber bundle, a television scanning element (e.g., a CCD array), or other imaging system. Such systems can include those that transport image information by optical means or are based on electrical or optical scanning systems. The detected image is observed at the proximal end of the endoscope 5 or at a remote location.

Figure 3:
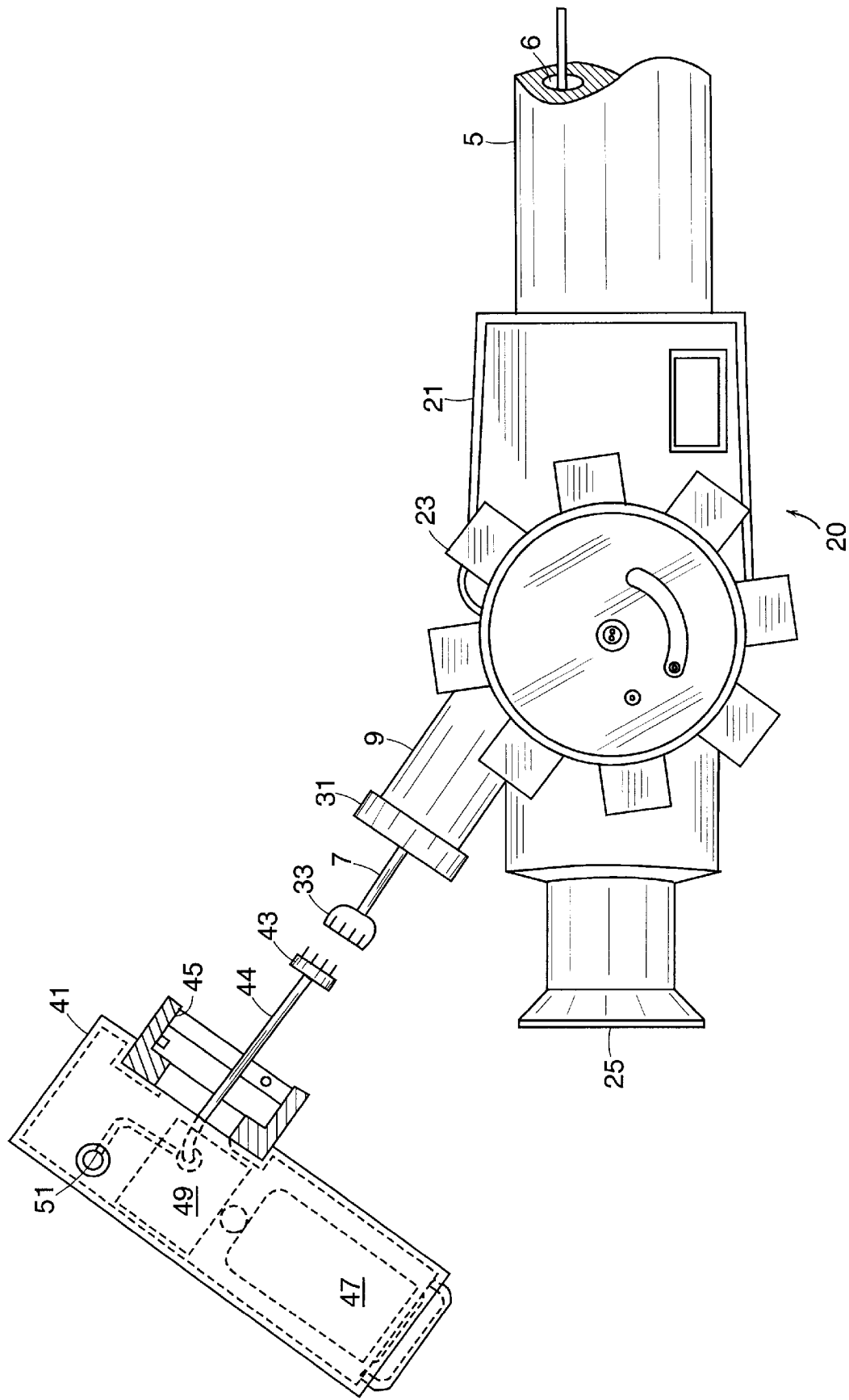
FIG. 3 is a side view of a control unit for a typical endofluorescence imaging module about to be mounted upon the proximal handle of an endoscope.

FIG. 3 is a side view of a control unit 41 for an endofluorescence imaging module mountable on the proximal handle 20 of the endoscope 5. An eyepiece 25 allows direct optical viewing of the image or is used as an attachment for a television or film camera. A working channel spout 9 provides convenient access to the working channel 6 that extends to the distal end of the endoscope 5. The control lines 7 extend from the working channel spout 9 and are terminated in a multipin connector 33. The multipin connector 33 is small enough to extend through the working channel 6 without impediment, thereby allowing the control unit 41 to be electrically connected with the distally mounted endofluorescence imaging module 3. A cable 44 having a connector 43 extends from the control unit 41 and mates with a connector 33 at the proximal end of the control lines 7. A flange 45 mates with a bayonet mount 31 for secure attachment of the control unit 41 in a convenient manner. The control unit electronics 49, which regulate electrical power and signals, is powered by a battery 47. A switch 51 on the control unit 41 actuates the control electronics 49.

Referring to FIG. 4A, an endofluorescence imaging module 3 includes a housing 100 which can be removably attached to the distal end of an interventional device. A light source 102 and a light modulator 104 are disposed in the housing 100. The light source 102 illuminates tissue within the body. The light source 102 can include, without limitation, a light emitting diode, a laser, a pulsed light source, a source of ultraviolet energy, or a flashlamp. The light modulator 104 modifies the light emitted by the light source 102. The light modulator 104 can include a filter providing a range of wavelengths to the optical channel of the interventional device. The filter can include, without limitation, an acousto-optic tunable filter, an interference filter, a grating, a prism, a holographic filter, a birefringent filter, or other component that provides a spectral passband. The light modulator 104 can also include a shutter. The shutter, for example, can comprise a liquid crystal device.

Figure 4B:
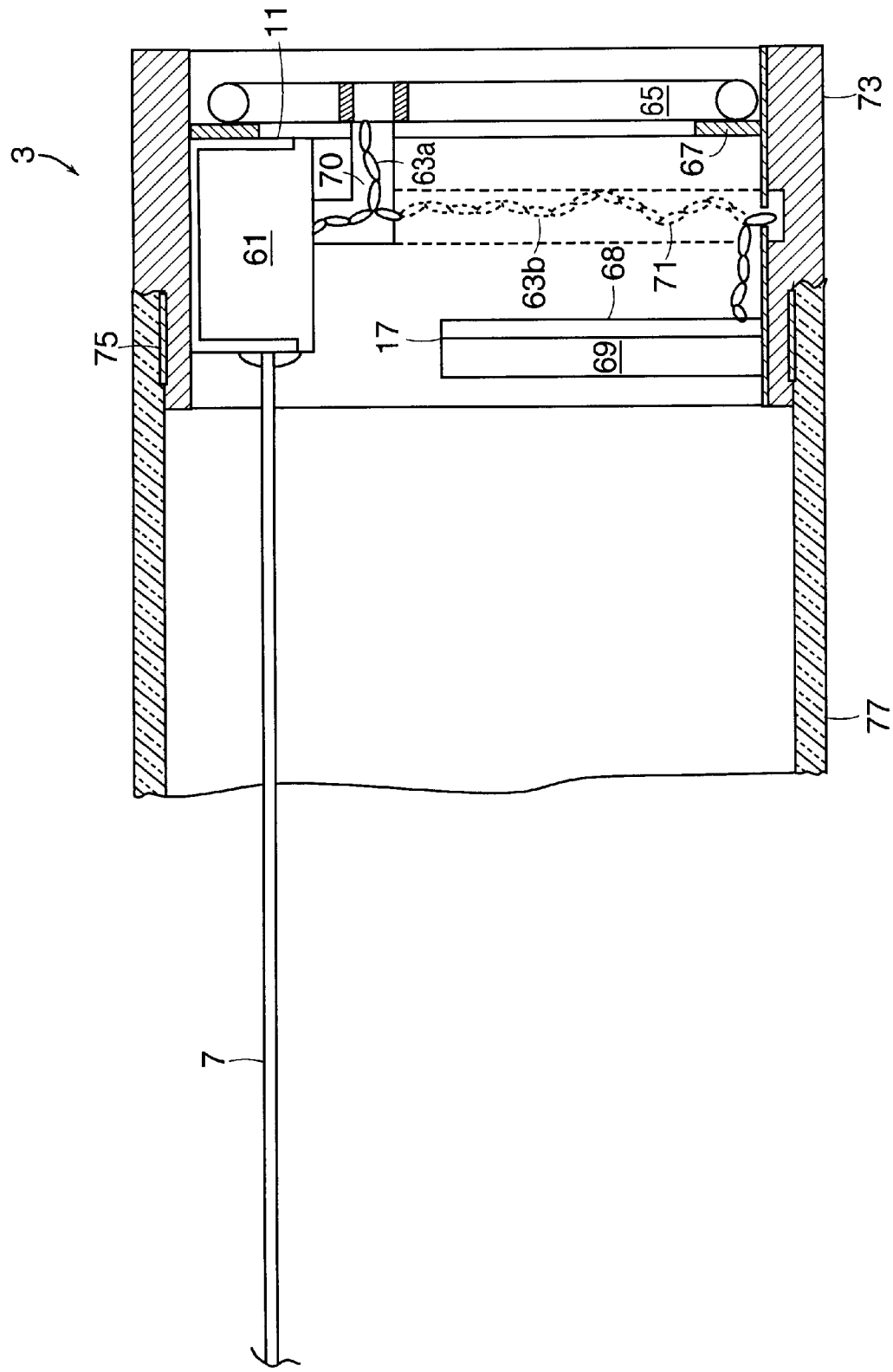
FIG. 4B is a detailed cross-sectional view of an endofluorescence imaging module showing a light source, a filter configuration, a light modulator and a control line mounted in a flexibly adaptable housing.

Referring to FIG. 4B, a detailed cross-sectional view of an endofluorescence imaging module 3 is shown. The control lines 7 terminate in the instrumentation mount 11 which holds transformer housing 61. Two wire pairs 63a and 63b extend from the transformer housing 61. The first wire pair 63a is disposed in a recess channel 70 and terminates at a circular xenon flashtube 65 held in place by mounting flange 67. The transformer (not shown) in the transformer housing 61 provides a voltage step up function for operation of the flashtube 65. The second wire pair 63b is disposed in a second recess channel 71 and terminates at a light modulator assembly 17. The light modulator assembly 17 includes a shutter 68 and a filter assembly 69.

Endofluorescence imaging module 3 has a rigid distal end section 73 made of a relatively rigid material, such as polystyrene, polycarbonate or polysulfone, and is colored or transparent. A urethane adhesive 75 secures the distal end section 73 to a flexible ring 77. The flexible ring 77 slides over the end of the endoscope 5 and provides secure attachment. Materials for this ring include elastomeric materials such as silicone, rubber, latex or polyurethane. Other plastics or fabrics can be used as long as the imaging module is securely attached to the endoscope 5 throughout the endoscopic procedure.

Figure 5:
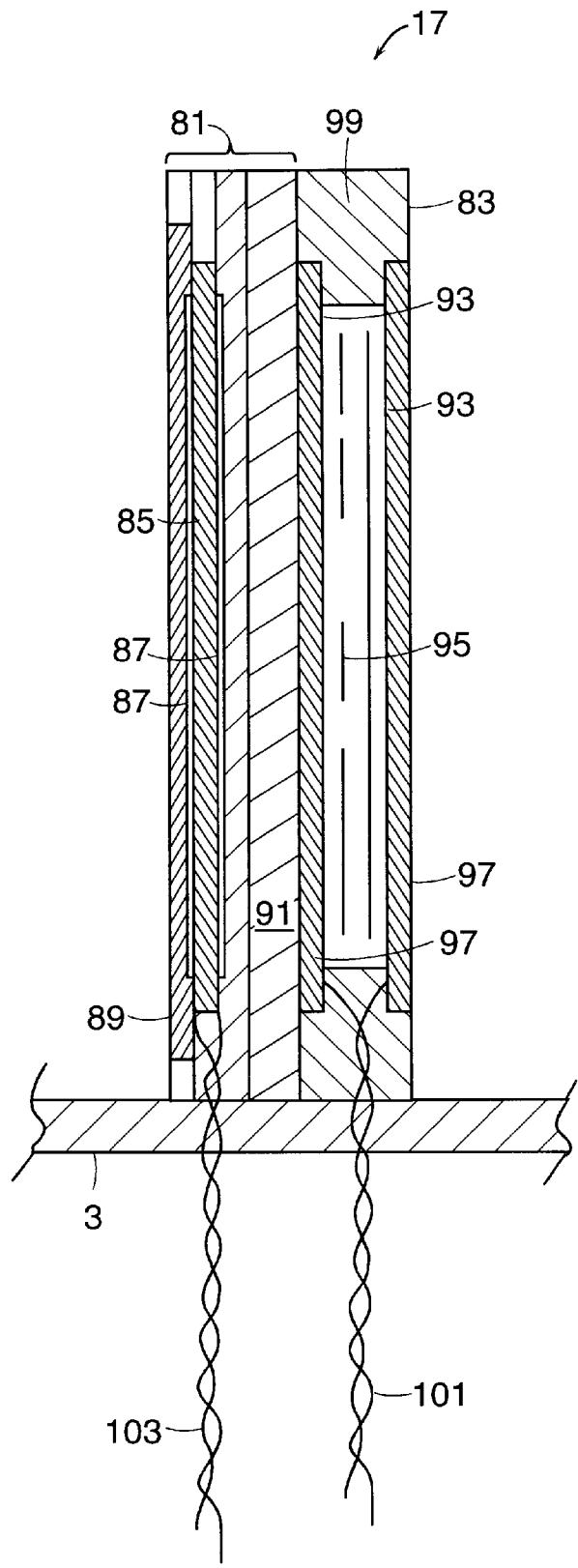
FIG. 5 is a detailed view of a light modulator assembly and filter configuration.

FIG. 5 shows a detailed light modulator assembly 17. A liquid crystal shutter 81 and an adjacent acousto-optic tunable filter (AOTF) 83 are mounted on a surface of the endofluorescent imaging module 3 with an adhesive. A metal mounting block 99 provides a mounting surface for the individual components of the shutter 81 and the AOTF 83. The AOTF control leads 101 and shutter control leads 103 extend through the recess channels 71 (shown in FIG. 4B). The liquid crystal shutter 81 includes a liquid crystal 85 located between two electrodes 87. The electrodes can be metalization layers on glass covers 89. When an electric field is applied between the electrodes 87 light passing through the liquid crystal 85 becomes polarized. A polarizing filter 91 is aligned for cross-polarization with the liquid crystal 85 in its active state. Therefore, when an electrical signal is applied to the electrodes 87, optical energy is prevented from passing to the optical channel 13 of the endoscope 5. An electrical signal can be applied for the duration of the optical pulse from the flashtube 65 in order to momentarily shutter the optical channel 13.

An electrical signal applied to both side electrodes 93 of the AOTF 83 changes the refractive index of the AOTF crystal 95 and polarizes the transmitted optical energy. Attenuation or selection of specific wavelengths is achieved when the AOTF crystal 95 is used in conjunction with polarizing filters 97. Voltage applied to the electrodes 93 controls the selected wavelength, allowing transmission of specific colors while rejecting other colors.

Operation of the endofluorescence imaging module 3 occurs after attachment to the interventional device. The flashtube 65 is fired in conjunction with actuation of the shutter 81 and is also be timed with the filter 83 to provide a temporary or repetitive fluorescence algorithm. The shutter 81 is used to temporarily block any white or colored light from entering the optical channel 13 during the firing of the flashtube 65.

The flashtube 65 can have an integral UV filter to attenuate all light outside UV wavelengths. A typical UV wavelength range of interest can include 290 nanometers to 370 nanometers. Red fluorescence that can occur can be effectively detected by endoscope 5 by tuning the AOTF 83 to a center wavelength of approximately 600 nanometers, thereby blocking all but the fluorescing signal. Blue fluorescence or UV fluorescence that may occur can also be detected if the AOTF 83 is tuned and timed in sequence with the onset and duration of the optical energy emitted from the flashtube 65.

Equivalents

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A diagnostic apparatus for use with an existing interventional device insertible in a body, comprising:
   a housing removably attachable to a distal end of the existing interventional device;
   at least one light source disposed in the housing for illuminating tissue within the body; and
   a light modulator disposed in the housing for modifying light emitted by the light source upon application of a control signal to the light modulator.

2. The diagnostic apparatus of claim 1 wherein the housing includes a flexible ring for securing to the distal end of the interventional device by an interference fit.

3. The diagnostic apparatus of claim 1 wherein at least a portion of the housing comprises an optically transparent material.

4. The diagnostic apparatus of claim 1 wherein at least a portion of the housing comprises a colored material.

5. The diagnostic apparatus of claim 1 wherein at least one of the light sources comprises a light emitting diode, a laser, a pulsed light source, or a source that emits ultraviolet energy.

6. The diagnostic apparatus of claim 1 wherein at least one of the light sources is a flashlamp.

7. The diagnostic apparatus of claim 1 wherein the light modulator modifies optical energy emitted from the tissue.

8. The diagnostic apparatus of claim 1 wherein the light modulator comprises a filter.

9. The diagnostic apparatus of claim 8 wherein the filter is an acousto-optic tunable filter, an interference filter, a grating, a prism, a holographic filter, or a birefringent filter.

10. The diagnostic apparatus of claim 8 further comprising a control unit attachable to the proximal end of the interventional device, the control unit providing electrical power and control signals to at least one of the light sources and the filter.

11. The diagnostic apparatus of claim 1 wherein the light modulator comprises a shutter.

12. The diagnostic apparatus of claim 11 wherein the shutter is a liquid crystal device.

13. The diagnostic apparatus of claim 1 further comprising a control unit attachable to the proximal end of the interventional device, the control unit providing electrical power and control signals to at least one of the light sources.

14. A diagnostic apparatus for use with an existing endoscope, comprising:
    a housing attachable to a distal end of the existing endoscope;
    at least one light source disposed in the housing for illuminating tissue; and
    a light modulator disposed in the housing, the light modulator comprising a shutter for controlling an exposure of an optical channel of the endoscope to optical energy emitted by the at least one light source, and the light modulator also comprising a filter for limiting a spectral wavelength range of an optical energy detected by the endoscope.

15. The diagnostic apparatus of claim 14 wherein at least one of the light sources is a flashlamp.

16. The diagnostic apparatus of claim 15 wherein the light modulator is responsive to a signal timed by an application of the flashlamp.

17. The diagnostic apparatus of claim 14 wherein the shutter is a liquid crystal device.

18. The diagnostic apparatus of claim 14 wherein the filter is an acousto-optic tunable filter.

19. A method for performing endofluorescence imaging of tissue in a body, comprising:
    attaching a housing to a distal end of an endoscope, the housing having at least one light source and a light modulator, the light modulator disposed in the housing for modifying light emitted by the light source upon application of a control signal to the light modulator; and
    illuminating the tissue using the at least one light source.

20. The method of claim 19 further comprising the step of spectrally filtering energy emitted from the tissue.

21. The method of claim 19 wherein the step of illuminating the tissue comprises transmitting pulses of optical energy.

22. The method of claim 19 further comprising the step of controlling an exposure of an optical channel of the endoscope to emitted optical energy.

23. A method for performing endofluorescence imaging of tissue in a body, comprising:
    attaching a housing to a distal end of an endoscope, the housing having at least one light source and a light modulator;
    illuminating the tissue with light generated from the at least one light source;
    spectrally filtering an optical energy emitted by the tissue;
    controlling an exposure of an optical channel of the endoscope to the light generated by the light source and the optical energy emitted by the tissue; and
    detecting the optical energy with the endoscope.

24. The method of claim 23 further comprising the steps of:
    providing a control unit having a power supply and control electronics;
    attaching the control unit to a proximal end of the endoscope; and
    providing electrical power and control signals to the at least one light source and the light modulator.

* * * * *